(12) United States Patent
Elliott

(10) Patent No.: US 7,067,632 B2
(45) Date of Patent: Jun. 27, 2006

(54) VP22 PROTEINS AND USES THEREOF

(75) Inventor: Gillian Daphne Elliott, Edenbridge (GB)

(73) Assignee: Phogen, Ltd., Cambridge (GB)

(*) Notice: Subject to any disclaimer, the term of this patent is extended or adjusted under 35 U.S.C. 154(b) by 0 days.

(21) Appl. No.: 10/617,910

(22) Filed: Jul. 10, 2003

(65) Prior Publication Data

US 2005/0118717 A1    Jun. 2, 2005

Related U.S. Application Data

(63) Continuation of application No. 09/381,211, filed as application No. PCT/GB98/00873 on Mar. 23, 1998.

(30) Foreign Application Priority Data

Mar. 21, 1997 (GB) ................... 9705903.4

(51) Int. Cl.
*A61K 38/00* (2006.01)
*A61K 38/16* (2006.01)
*C07K 14/00* (2006.01)

(52) U.S. Cl. ............... 530/350; 530/300; 530/402; 514/2

(58) Field of Classification Search ........... 530/300, 530/350, 402; 424/185.1, 192.1, 204.1, 235.1; 435/69.1, 69.7; 514/2
See application file for complete search history.

(56) References Cited

U.S. PATENT DOCUMENTS

| | | | |
|---|---|---|---|
| 4,942,184 A | | 7/1990 | Haugwitz et al. |
| 5,272,171 A | | 12/1993 | Ueda et al. |
| 5,356,927 A | | 10/1994 | Taraschi et al. |
| 5,583,153 A | * | 12/1996 | Brahn .................. 514/449 |
| 5,621,001 A | | 4/1997 | Canetta et al. |
| 5,631,278 A | | 5/1997 | Taraschi et al. |
| 6,017,735 A | * | 1/2000 | O'Hare et al. ............ 435/69.7 |
| 6,184,038 B1 | * | 2/2001 | O'Hare et al. ............ 435/455 |
| 6,251,398 B1 | * | 6/2001 | O'Hare et al. ............ 424/186.1 |

FOREIGN PATENT DOCUMENTS

| | | |
|---|---|---|
| EP | 0 473 326 | 3/1992 |
| EP | 0 505 047 | 9/1992 |
| EP | 0 537 905 | 4/1993 |
| EP | 0 558 959 | 9/1993 |
| EP | 0 584 001 | 2/1994 |
| WO | WO 89/08453 | 9/1989 |
| WO | WO 90/10443 | 9/1990 |
| WO | WO 93/02065 | 2/1993 |
| WO | WO 93/14787 | 8/1993 |
| WO | WO 94/12172 | 6/1994 |
| WO | WO 97/05265 | 2/1997 |

OTHER PUBLICATIONS

"Herpesvirisdae", MeSH Browser, www.ncbi.nlm.nih.gov/entrez/query.fcgi?db=mesh.*
Entry for "herpesvirus", The On-line Medical Dictionary, cancerweb.ncl.ac.uk/omd/.*
Benet et al., *The Pharmacological Basis of Therapeutics*, 8th ed., pp. 3-266, McGraw Hill, Inc., New York, New York, 1990.
De Arruda et al., *Cancer Research* 55(14):3085-3092, 1995.
Dermer, *Bio/Technology* 12:320, 1994.
Elliott et al., *J. Gen. Virol.* 73:723-726, 1992.
Elliott et al., *Cell* 83:223-233, 1997.
Jain, *Cancer Research and Metastasis Reviews* 9:253-266, 1990.
Jain, *Science* 271:1079-1080, 1996.
Mandelkow et al., *Neurobiology of Aging* 16(3):355-363, 1995.
Marshall et al., *Nature Biotechnology* 15(3):205, 1997.
Piperno et al., *J. Cell Biol.* 104:289-302, 1987.

* cited by examiner

Primary Examiner—James C. Housel
Assistant Examiner—Zachariah Lucas
(74) Attorney, Agent, or Firm—Klarquist Sparkman LLP

(57) ABSTRACT

Herpesviral VP22 proteins (and variants) are used to modify cell structure and cell division, by their newly found property of binding to microtubules in cells. Uses of VP22 to exploit this property include stabilisation of animal cellular microtubules in vivo and in vitro, e.g. to retard or arrest cell division or induce cell death. The microtubule binding function of VP22 can be exploited by reagent use in vitro to study microtubules or the cell cycle particularly at cell division, and pharmaceutically to retard or arrest cell division of cells such as neoplastic cells or protozoal parasite cells in vitro or in vivo.

5 Claims, 3 Drawing Sheets

VP22 PROTEINS AND USES THEREOF

PRIORITY CLAIM

This is a continuation of U.S. application Ser. No. 09/381,211, filed Sep. 17, 1999, which is a § 371 U.S. national stage of PCT/GB98/00873 filed Mar. 23, 1998, which was published in English under PCT Article 21(2), which in turn claims priority from Great Britain Patent Application No. 9705903.4, filed Mar. 21, 1997. The prior applications are all incorporated by reference herein.

FIELD OF THE INVENTION

This invention relates to uses of VP22 proteins (and of its variants) e.g. for modifying cell structure and cell division. The invention also relates to variants of VP22 proteins, e.g. active portions and derivatives. The invention relates further to compositions comprising VP22 proteins and to methods and materials for producing them, including without limitation polynucleotides and recombinant cells and vectors encoding them.

BACKGROUND OF THE INVENTION

The product of the herpes simplex virus type 1 (HSV 1) UL49 gene, the structural protein VP22 (Elliott et al, J. Gen. Virol., 73:723–6), is a major component of the HSV tegument, a compartment of the virion located outside the capsid and inside the envelope and composed of at least 10 or more additional virus polypeptides. VP22 has a molecular weight of 32 kD, is very basic and is modified by phosphorylation and nucleotidylation in the infected cell.

Despite being one of the major tegument proteins within the virion, together with the well characterised transcription regulatory protein VP16, much remains to be discovered about the function of VP22 during the virus replicative cycle. It is not yet known if it is an essential virus protein, but it is possible that, in a manner similar to VP16, VP22 has more than one role to perform during infection—initially as a functional protein during viral gene expression, and subsequently as a structural component of the virion during virus assembly. As regards the former, some evidence exists to suggest that VP22 can bind specifically to HSV 1 DNA.

In International patent application WO 97/05265 (O'Hare and Elliott) (incorporated herein by reference), it is disclosed inter alia that when the HSV 1 protein VP22 is expressed by transfection in mammalian cells, it exhibits a series of unusual properties. Firstly, the protein spreads between cells, so that when VP22 is expressed in a group of cells, it is secreted and delivered to the nuclei of other cells in the population not initially transfected. Secondly, in cells in which VP22 is expressed, it is present in a cytoplasmic filamentous pattern. The application further discloses that the transport property related to the secretion and delivery is associated with a determinant in the C terminal 34 amino acids of VP22. Applications of the transport property of VP22 disclosed in WO 97/05265 include associating molecules with VP22 so that they are transported to a target population of cells, either by expression of VP22, or an active fragment thereof, and the associated molecule as a fusion protein in some of the cells in the population, or by coupling VP22, or an active fragment thereof, to the associated molecule and exposing a population of cells to the VP22 complex directly.

SUMMARY AND DESCRIPTION OF THE INVENTION

The present invention is related to a new finding that herpesviral VP22 protein, particularly for example the VP22 protein of HSV1, has the property of binding to microtubules in cells. The present invention provides uses of VP22 that exploit this property, and further relates to variant VP22 molecules lacking or modified for reduction in potency of this property, and to their uses. It has been observed in particular, that in cells in which VP22 is expressed, the VP22 protein that is not secreted binds to cellular microtubules (MTs) in a cytoplasmic filamentous pattern.

According to aspects of the present invention, therefore, VP22 can be employed in applications such as stabilising MTs and retarding cell growth, in the delivery of MT binding drugs, and in gene or protein delivery in which MT associated transport is required. In this first context, VP22 means a protein which has sequence homology with VP22 and has a microtubule binding function of VP22.

Thus the invention provides use of herpesviral VP22 protein or of another protein which has sequence homology with VP22 and a microtubule binding function of VP22, or a derivative thereof, to stabilise animal cellular microtubules, and also provides methods of retarding or arresting growth and cell division, or of inducing cell death, of an animal cell which comprises exposing said cell to herpesviral VP22 protein or of another protein which has sequence homology with VP22 and a microtubule binding function of VP22, or a derivative thereof, in an amount effective to stabilise the microtubules of said cell.

Particular examples of such use include methods of using herpesviral VP22 protein or of another protein which has sequence homology with VP22 and a microtubule binding function of VP22, or a derivative thereof, in an effective amount to retard or inhibit the cell division of animal cells, e.g. in antineoplastically effective amounts to retard or inhibit the cell division of neoplastic cells in vitro or in vivo, e.g. melanoma cells, ovarian cancer cells, or leukemia cells among others. The uses for VP22 provided hereby also include use for increasing the sensitivity of cells to cytotoxic effects of ionising radiation, in effective cytotoxic dose of radiation.

Further examples of such use include use in amounts effective to inhibit cell proliferation and/or induce cell death of other animal cells, e.g. cells of protozoal parasites, e.g. in vitro or in vivo.

In further aspects of the invention herpesviral VP22 proteins and other proteins with sequence homology with VP22 and a microtubule binding function of VP22, or derivative thereof, can be used for delivery also of other microtubule-binding drugs, e.g. taxol or its derivatives, or colchicine.

For these ands other purposes the invention also provides use of herpesviral VP22 protein or of another protein which has sequence homology with VP22 and a microtubule binding function of VP22, or a derivative thereof, in the preparation of medicaments for delivery of substances to cell microtubules.

The derivative can be a coupling product comprising VP22 and another substance to be delivered to the microtubules.

VP22 can be used, e.g. in amounts effective to stabilise microtubules and/or to enhance their degree of acetylation (as described below) and/or to inhibit the cells from progressing through the G2 and M phases of the cell cycle, not only for pharmaceutical effect but also as reagents in-vitro to study microtubules or the cell cycle particularly at cell division. For the purposes of reagent use in vitro such a derivatives can be a fusion protein between VP22 and an indicator protein, e.g. a fusion protein between VP22 and green fluorescent protein.

In a further aspect of the invention, the initial localisation of the determinant in VP22 responsible for binding to the microtubules makes it possible to use protein engineering to provide and make variants of herpesviral VP22 proteins that have a reduced tendency to bind to microtubules, or even substantially lack this property altogether, but retain the useful transport property of VP22.

Thus the invention also provides variants of herpesviral VP22 proteins that possess the transport property and function described in specification WO 97/05265 but have a reduced tendency to bind to microtubules, compared with the native protein. In this further context, VP22 means a protein which has the transport property and function described in specification WO 97/05265.

Cellular microtubules (MTs) are polymers of heterodimers composed of alpha-and beta-tubulin. They form networks within the cytoplasm and perform several functions for the cell, including the trafficking of organelles and vesicles, the movement of chromosomes during mitosis, and the general organisation of the cytoplasm and maintenance of cell architecture. MTs are dynamic structures, which grow from a central MT organising centre (MTOC) out towards the periphery of the cell. These dynamics are important during cell division when the MTs depolymerise to form the spindle poles. As such, inhibition of MT depolymerisation can lead to retarded cell division. Therefore, they are targets for the treatment of proliferative disorders such as cancer.

Thus in one aspect, the invention provides methods and compositions for treating cells with a VP22 protein, thereby to stabilise the microtubules in said cells: the invention extends to methods of using VP22 in the manufacture of such compositions.

Such methods can be usefully carried out in vitro or in vivo. As an example of an in vitro method, the VP22 protein can be used in the form of a coupling product with an indicator protein such as green fluorescent protein (described in WO 97/05265), and such a coupling product can be used for example as a tool for the microscopic examination of MT reorganisation in the cell cycle in live cells in vitro.

In relation to the in vivo uses, the present invention also provides the use of VP22, or an active portion or derivative thereof having the property of binding to microtubules, in the preparation of a medicament for stabilising microtubules in a population of cells.

This stabilisation can have the effect of directly retarding the growth of cells, and be useful in the treatment of proliferative disorders such as cancer. Alternatively, the stabilisation of the microtubules against agents that depolymerise microtubules can be used to protect a portion of a population of cells from the effects of these agents, e.g. while diseased cells in the population are treated. Examples of such agents include nocodazole, colecemid (used in anti fungal therapy) or vinblastine and derivatives thereof (used in anti-cancer therapy).

In both of the above applications, the known transport property of VP22 can be used to deliver the VP22 to the cells to stabilise the MTs, either by expressing nucleic acid encoding VP22 in at least a portion of the cells in the population or by directly exposing the cells to VP22 protein.

In a further aspect, the present invention provides the use of VP22, or an active portion or derivative thereof having the property of binding to microtubules in the preparation of a medicament for delivery of a substance to the microtubules, e.g. by the use of a coupling product comprising VP22 and the substance to be delivered to the MTs.

In some embodiments, VP22 can be targetted to a cell in conjunction with a further MT binding substance such as taxol or a derivative thereof, or colchicine. VP22 can also be used to deliver the further MT binding substance to the MTs, helping to enhance the activity of the substance and/or to allow a reduced dose of the substance to be used in the treatment of a patient.

Examples of further MT binding substances are chemotherapeutic agents such a taxol or derivatives thereof which retard cell growth by binding to MTs. Some of these substances can have severe side effects, thus enhancing the activity of the substances and/or reducing the dose required in a given situation can be useful.

Accordingly, one aspect of the invention provides a coupling product between a VP22 protein and a therapeutic agent that affects assembly or disassembly of MTs. An example is a coupling product between VP22 and a taxol or related compound which can be made using per se known chemical coupling methods. A further example is a coupling product between a VP22 protein and colchicine. The invention also extends to the use of such coupling products. Amongst the uses of these particular coupling products are that they can be useful as tools to study the cell cycle particularly at cell division.

It can be seen that the invention also provides uses of VP22 proteins, and of their variants which possess MT binding function, in ways analogous to the uses known for MT binding substances such as taxol, and the resulting materials can be used if desired in conjunction with other MT binding substances. Delivery of VP22 to target cells for the purposes described herein can if desired be achieved through the use of corresponding gene vectors as described in WO 97/05265, and the uses of such vectors including recombinant virus vectors, and nonviral vectors such as lipofection or transfection by naked DNA, such as herpesviral vectors carrying modified forms of VP22, are within the scope of the ivnention.

Taxol and related compounds, and their uses adaptable by and applicable to this invention, include for example the substances and derivatives related to taxol and their uses, as described in WO 89/08453 and U.S. Pat. No. 4,942,184 (R Haugwitz et al: US Secretary of State of Commerce) (describing water-soluble derivatives of taxol and their cytotoxic and anti-neoplastic uses); WO 90/10443 (V Stella et al: Univ Kansas); EP 0 537 905, EP 0 473 326, and EP 0 505 047 (DGI Kingston et al: Virginia Tech); and EP 0 524 093, WO 93/02065 (JD Bourzat et al: Rhone Poulenc Rorer SA); and EP 0 558 959 and U.S. Pat. No. 5,272,171 (Y Uedai et al: Bristol Myers Squibb) (describing derivatives of taxol and uses for anti-mammalian tumor activity).

Uses of coupling products between taxol and VP22, and compositions comprising them can include for example uses and compositions analogous to those described in the following cited documents:

use for increasing the sensitivity of cells to cytotoxic agents such as ionising radiation, by analogy with WO 93/14787 (PB Schiff: Columbia Univ) (describing exposure of cells to taxol in amounts effective to inhibit the cells from progressing through the G2 and M phases of the cell cycle and then exposing the cells to a cytotoxic agent such as radiation or bleomycin);

use for inhibiting proliferation of protozoa such as protozoal parasites, by analogy with WO 94/12172, U.S.

Pat. No. 5,631,278 and U.S. Pat. No. 5,356,927 (TF Taraschi et al: Thomas Jefferson Univ); and infusion treatment of subjects carrying malignancy, by analogy with EP 0 584 001 and U.S. Pat. No. 5,621,001 (RM Canetta et al: Bristol Myers Squibb) (describing administration to a subject having cancer, e.g. ovarian cancer, by a procedure comprising infusion over a period of 6 hours or less at a dose rate of about 135 mg/m2).

The delivery of the MT binding materials to MTs can be a step in the transport of the substance to other types of cells. By way of example, MT associated transport is believed to be involved in the neuronal transport of substances. Thus, by associating a substance such as nucleic acid or a protein with the VP22, transport of the substance to such cells can be achieved by virtue of the VP22 binding to the MTs.

Generally, the VP22 protein or fragment thereof can be coupled to the coupling partner by chemical or recombinant DNA techniques.

In this aspect of the invention, the coupling partner substance, where it is a polypeptide, can preferably be expressed as a fusion with the VP22. Preferred embodiments include fusion proteins each resulting from expression in a recombinant host cell of a polynucleotide sequence of which part encodes part of all of the amino acid sequence of the VP22 protein and another part encodes part or all of the amino acid sequence of a coupling partner polypeptide.

In these embodiments, the nucleic acid encoding the fusion protein only needs to be transfected into a portion of cells in a population as the VP22 fusion is secreted and taken up into untransfected cells. In the cells transformed with VP22, its expression can be controlled using tissue specific or inducible promoters.

Alternatively, the VP22 and the substance can be covalently coupled or non covalently associated, e.g. using lipid based vehicles, and directly exposed to the target cells. In particular, this allows non peptidyl molecules, such as nucleic acid, drugs or markers (in addition to or as alternatives to proteins) to be associated with VP22 and be taken up into a population of cells, without the need to express the VP22 and the associated molecule in at least a part of the population of cells to which delivery of the VP22 and/or the associated molecule is desired.

In certain embodiments the partner can be coupled by chemical crosslinking, in per se known manner, e.g. by standard techniques involving covalent attachment for example to exposed tyrosine residues of the VP22 protein or to the epsilon-amino groups of lysine residues or the carboxyl groups of aspartate and glutamate residues.

In a further aspect, the present invention provides VP22 variants having a transport property associated with full length VP22, but which are substantially incapable of binding to microtubules. These VP22 variants can be based on the insertion, addition, deletion or substitution of one or more amino acids in the region of VP22 corresponding to amino acid residues 119 to 192 to reduce or eliminate VP22 binding to microtubules, while retaining another biological activity of VP22 such as the transport property. One such example with much reduced MT binding is provided by e.g. a VP22 deletant in respect of aminoacids 160–173 of VP22 of HSV1, Other examples can also be provided by varying the amino acid sequence of the VP22 protein, e.g. by manipulation of the nucleic acid encoding the protein or by altering the protein itself. By way of example, non conservative alteration of the VP22 amino acid sequence at one or more amino acid residues in a region of VP22 associated with MT binding activity, e.g. aminoacid residues 160–173 of VP22 of HSV1, can be used to reduce or eliminate that activity. Alternatively, the VP22 variants can be engineered to reduce or eliminate the MT binding activity by modification elsewhere in the molecule, where such modification results in the disruption of the determinant of VP22 responsible for MT binding.

In cells expressing VP22, binding of the protein to MTs prevents this portion of the VP22 from being secreted and serving as a transport protein, e.g. where the VP22 is expressed as a fusion with a protein for delivery to other cells. Accordingly, engineering variants of VP22 that lack the MT binding property, but which retain the transport property can be usefully employed to improve the efficiency of the transport, where MT binding is not required.

In a further aspect, the present invention provides the use of VP22 variants as defined above as transport proteins, in ways analogous to the uses and properties of VP22 out in application WO97/05265.

BRIEF DESCRIPTION OF THE FIGURES

The present invention is further described by way of example with reference to the accompanying Figures, in which:

FIGS. 1c and 1d show the effect of adding taxol to the COS-1 cells expressing VP22 as compared to untransfected cells.

FIGS. 2c and 2d show the effect of nocodazole to the VP22 cell line and the control.

Figure 1:
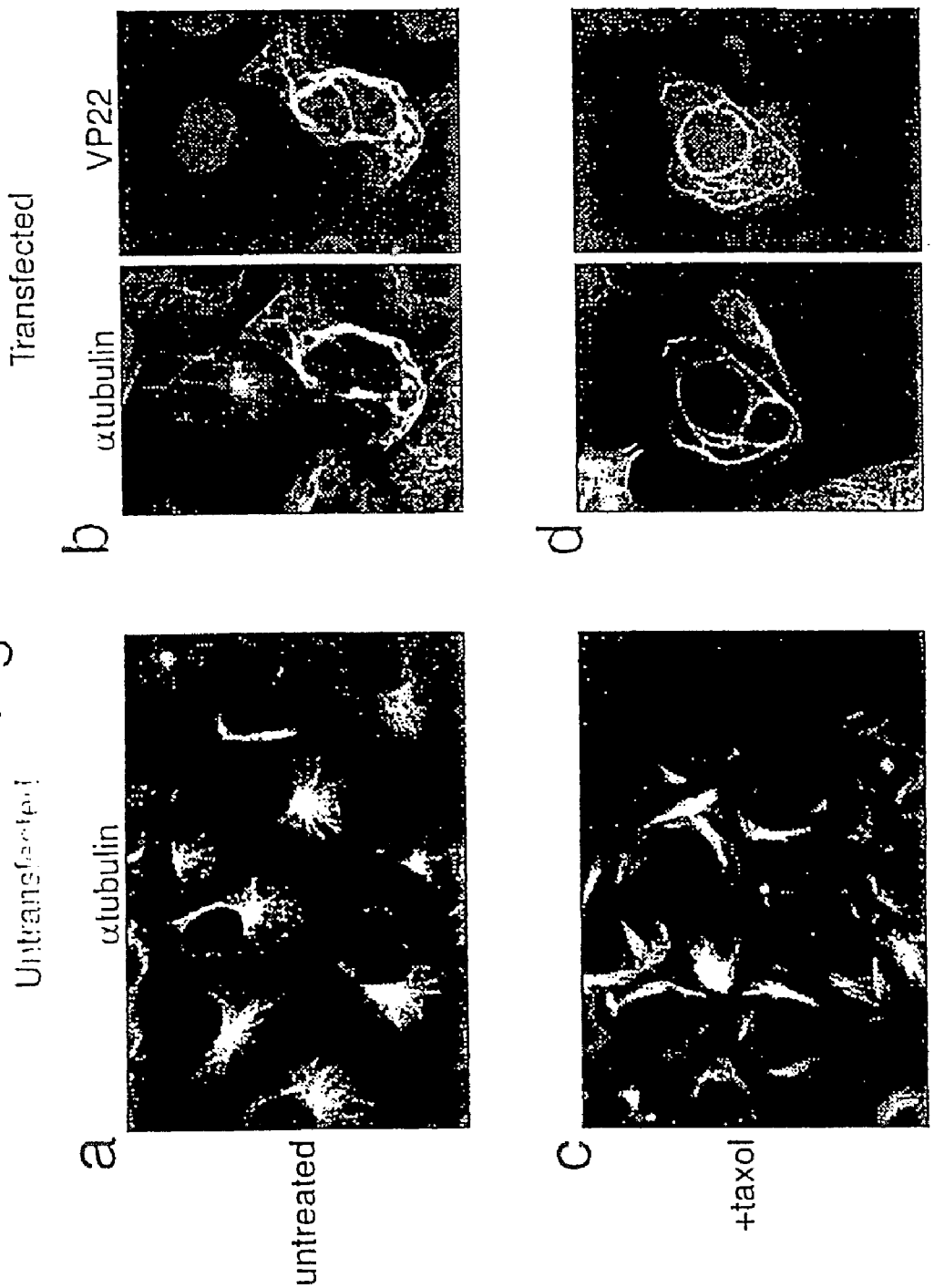
FIG. 1 shows the localisation patterns of VP22 and MTs obtained using COS-1 cells expressing VP22 as compared with untransfected cells. The localisation patterns were produced by immunofluorescence using anti alpha-tubulin and VP22 antibodies.

An active portion of the VP22 polypeptide means, in the context of those parts of this specification in which proteins having microtubule-binding functionality are of concern, a peptide that comprises less than the full length sequence of VP22 (and optionally comprises further sequence, e.g. not derived from the sequence of VP22 but from the sequence of a polypeptide fusion coupling partner) but which retains a property of binding to microtubules.

Derivatives of VP22 polypeptides considered within the scope of thois specificaiton include polypeptides modified by varying the amino acid sequence of the VP22 protein, e.g. by manipulation of the nucleic acid encoding the protein or by altering the protein itself after it has been synthesised. Such derivatives of the natural amino acid sequence can involve insertion, addition, deletion or substitution of one or more amino acids.

VP22 polypeptides which are derivatives or sequence variants will generally have greater than about 70% sequence homology with the amino acid sequence of a wild type VP22 sequence, e.g. that of HSV1, and preferably shares greater than about 80%, greater than about 90% or greater than about 95% sequence homology.

Particular amino acid sequence variants can differ by insertion, addition, substitution or deletion e.g. of 1 amino acid, 2, 3, 4, 5 10, 10 20 20 30, 30 50, 50 100, 100 150, or more than 150 amino acids.

The variants considered within the scope of the present specification include those with conservative alterations in the VP22 amino acid sequence, i.e. with alterations resulting in residues having similar charge and/or structure at the position or positions being altered. Typically, conservative alteration does not in itself fundamentally alter a biological activity of VP22 protein, e.g. MT binding activity.

The variants considered within the scope of the present specification also include those with non-conservative alterations, i.e. alterations resulting in residues having substantially different charge and/or structure at the positions being altered. Non conservative alterations can be made to change a biological activity of the protein, e.g. to abolish a given activity (e.g. MT binding) or provide a biological activity that is substantially absent from the starting protein.

The amino acid classes considered in the foregoing discussion comprise two main groups, charged and uncharged, and each of these groups is divided into subgroups, usually considered to be as follows: Among charged amino acids, basic residues are lysine, arginine, and histidine. Acidic residues are aspartic acid, and glutamic acid. Among uncharged amino acids are hydrophilic residues glutamine, serine, threonine, and asparagine, and aliphatic residues alanine, glycine, valine, leucine, and isoleucine; as well as non polar residues cysteine, methionine, and proline, and aromatic residues phenylalanine, tyrosine, and tryptophan.

In the present invention, the biological property of binding to MTs can be determined using antibodies against VP22, or the active portion or derivative, and commercially available anti alpha- or beta-tubulin antibodies. Thus, labelling the antibodies (e.g. using immunofluorescence) and comparing the patterns obtained when the antibodies bind to the cells in the test, makes it possible to determine whether the antibodies are co localised in the cells.

It has also been found that the stabilisation of MTs by VP22 is associated with acetylation of the MTs. Acetylation of MTs was previously reported as a marker for MT stability (Piperno et al, J Cell Biol 104 (1987) 289–302). This has been shown by use of monoclonal antibody specific for the acetylated form of tubulin (obtainable from Sigma Chemical), in colocalisation assays by immunofluorescence, and by Western blot assays. This effect can be used as a biochemical marker for analysing and quantitating the level of MT stabilisation induced by VP22 or a variant or derivative thereof.

It has further been found that a fusion between VP22 and green fluoresecent protein (GFP), as described in WO 97/05265, is also, like wild-type VP22 protein, capable of stabilising MTs, thus allowing convenient fluorescence monitoring procedures including fluorecence microscopy to monitor the MT stabilisation and its effects.

Alternative protocols can be readily determined by the skilled person by adapting and using per-se routine techniques known in the art.

The peptide determinant of VP22 responsible for MT binding can be further refined using and adapting techniques well known per se in the art. This can be done by systematically varying the amino acid residues in the peptide, e.g. by substituting each residue in turn. These parts or residues constituting the active region of the compound are known as its pharmacophore.

By way of example, alanine scans take peptide fragments from a region of the full length protein associated with a biological activity and replace the amino acids with alanine. If the substitution of a given residue for alanine reduces or eliminates the biological activity, it shows that residue is important or critical for that biological activity. Repeating this helps to define the amino acids that are responsible, e.g. for the MT binding of VP22. Other techniques that can be used to resolve motif in VP22 protein include deletion series, site directed mutagenesis, and yeast two-hybrid screening.

The VP22 proteins of the invention, including coupling products and VP22 variants can be formulated in pharmaceutical compositions. The compositions can comprise, in addition to one of the above VP22 proteins, a pharmaceutically acceptable excipient, carrier, buffer, stabiliser or other materials well known to those skilled in the art. Such materials should be non toxic and should not interfere with the efficacy of the active ingredient. The nature of the carrier or other material can depend on the desired route of administration, e.g. oral, intravenous, cutaneous or subcutaneous, nasal, intramuscular, intraperitoneal routes.

Pharmaceutical compositions for oral administration can be in tablet, capsule, powder or liquid form. A tablet can include a solid carrier such as gelatin or an adjuvant. Liquid pharmaceutical compositions generally include a liquid carrier such as water, petroleum, animal or vegetable oils, mineral oil or synthetic oil. Physiological saline solution, dextrose or other saccharide solution or glycols such as ethylene glycol, propylene glycol or polyethylene glycol can be included.

For intravenous, cutaneous or subcutaneous injection, or injection at the site of affliction, the active ingredient will be in the form of a parenterally acceptable aqueous solution which is pyrogen free and has suitable pH, isotonicity and stability. Those of relevant skill in the art are well able to prepare suitable solutions using, for example, isotonic vehicles such as sodium chloride Injection, Ringer's injection, lactated Ringer's Injection. Preservatives, stabilisers, buffers, antioxidants and/or other additives can be included, as desired.

When the pharmaceutical compositions provided and used according to the present invention are given to an individual subject of treatment, administration is preferably in a prophylactically effective amount or a therapeutically effective amount (as the case may be, prophylaxis can be considered therapy), this being sufficient to show benefit to the individual. The actual amount administered, and rate and time course of administration, depends on the nature and severity of what is being treated. Prescription of treatment, e.g. decisions on dosage etc, is within the responsibility of medical practitioners and typically takes account of the disorder to be treated, the condition of the individual patient, the site of delivery, the method of administration and other factors known to practitioners. Examples of techniques and protocols as mentioned above can be found in Remington's Pharmaceutical Sciences, 16th edition, Osol, A. (ed), 1980. A composition can be administered alone or in combination with other treatments, either simultaneously or sequentially dependent upon the condition to be treated.

Experimental

The following experiments demonstrate that VP22 binds to MTs in cells, localising in a similar way to a known MT binding agent, taxol. Further experiments show that VP22 can stabilise MTs against the action of depolymerising agents and investigate the portion of VP22 associated with the MT binding activity.

The description and experiments set out below illustrates background and techniques which are applicable to the assessment of the the VP22 variants, compositions, methods and uses according to the invention. The skilled person could apply these techniques, e.g to determine whether VP22 proteins or variants thereof have the biological property of binding to and/or stabilising MTs.

VP22 Binds to Microtubules in COS 1 Cells.

Cellular microtubules (MTs) are polymers of heterodimers composed of alpha and beta tubulin. They form networks within the cytoplasm and perform several functions for the cell, including the trafficking of organelles and vesicles; the movement of chromosomes during mitosis; and the general organisation of the cytoplasm and maintenance of cell architecture. MTs are dynamic structures, which grow from a central MT organising centre (MTOC) out towards the periphery of the cell. These dynamics are important during cell division when the MTs depolymerise to form the spindle poles. As such, inhibition of MT depolymerisation can lead to retarded cell division.

To investigate the possibility that the pattern of localisation in cells expressing VP22 represents co-localisation with a component of the cytoskeleton, COS 1 cells were transfected with the VP22 expression plasmid pGE109. Forty hours after transfection, the cells were fixed with 100% methanol and double immunofluorescence carried out with antibodies against VP22 (polyclonal AGV30) and alpha tubulin (monoclonal anti alpha tubulin, Sigma).

Untransfected cells labelled in the same manner exhibited the typical localisation pattern for MTs (FIG. 1a) with the MT network radiating from the MTOC. However, cells expressing VP22 had a very different MT pattern where the tubules were bundled and co localised with the VP22 filaments (FIG. 1b). COS 1 cells treated in the same manner were exposed to the MT stabilising drug taxol (10 microM) for 30 minutes prior to fixation. In untransfected cells, taxol has the effect of creating large bundles of MTs (FIG. 1c). In VP22 expressing cells, these bundles were even more striking and again co-localised with VP22 (FIG. 1d). Taken together, these results show that VP22 colocalises and reorganises the cellular MT network into bundles. This shows that VP22 can be used in the compositions and methods of the invention to bind to MTs. The MT binding property of VP22 can also be used to deliver coupling products between VP22 and other substances, such as taxol or a related compound to MTs.

VP22 Stabilises Microtubules Against Depolymerising Agents.

When MTs are bundled as observed above, they are often stabilised against depolymerising agents. To test if VP22 bundling of MTs also stabilises these filaments, COS 1 cells were transfected as before, and then exposed to the drug nocodazole (500 ng/ml), an agent known to depolymerise MTS, for 30 minutes prior to fixation. The cells were then fixed and processed for immunofluorescence using only the anti alpha tubulin antibody.

Figure 2:
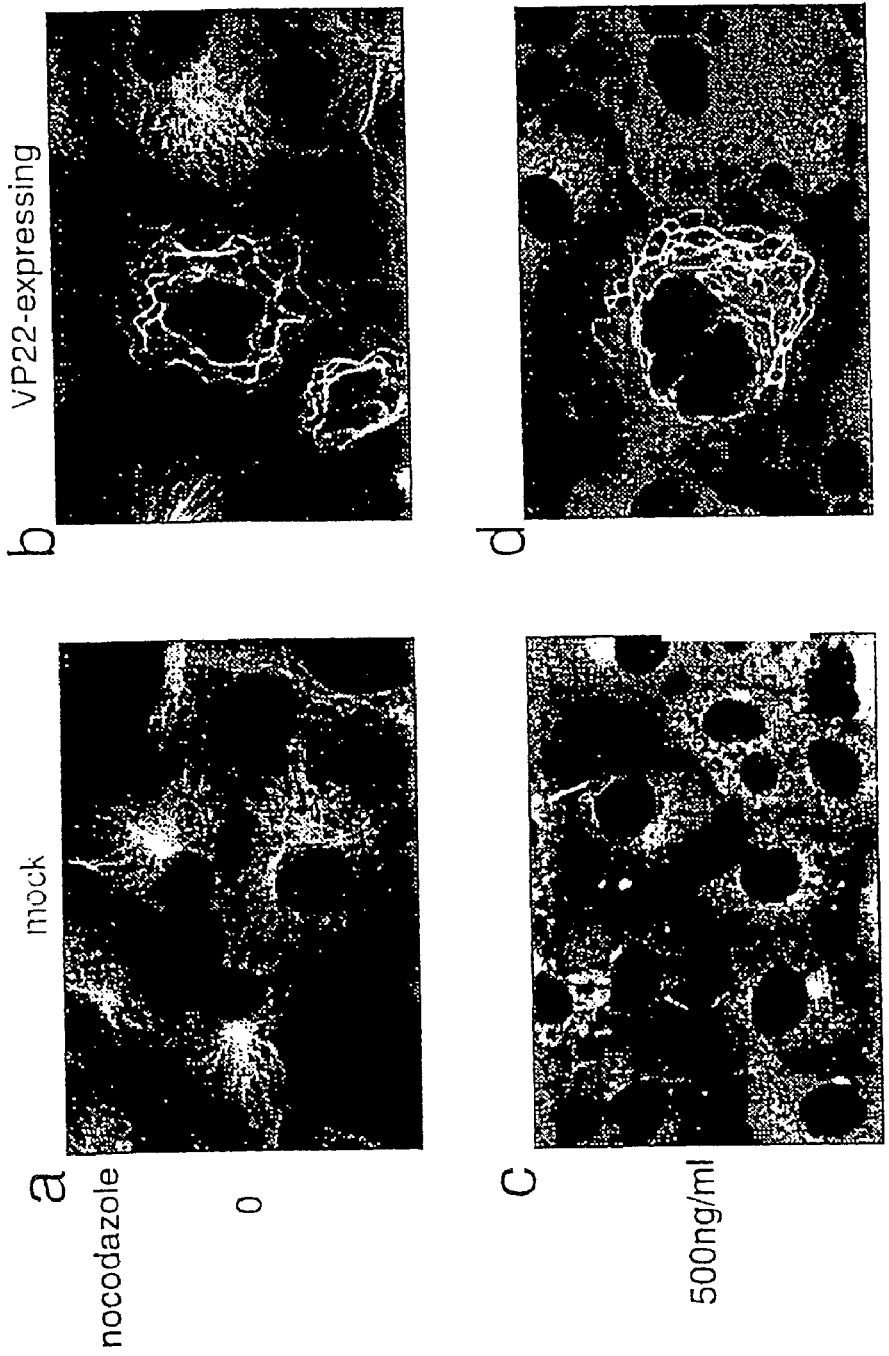
FIG. 2 shows the localisation patterns obtained using immunofluorescence with anti-alpha-tubulin antibody in a COS-1 cell line expressing VP22 and a control.

In the control tests, in the absence of nocodazole treatment the MT network of VP22 expressing cells is easily distinguished in comparison to untransfected cells; see FIG. 2, compare a and b. Nocodazole treatment of untransfected cells results in the depolymerisation of the MT network (FIG. 2c). However, the same treatment of VP22 expressing cells does not depolymerise the MTs, which remain in a similar pattern to that seen in untreated cells (FIG. 2d).

Thus, VP22 can stabilise MTs against depolymerising agents. The same effect was seen upon incubation of cells at 4 deg C., a treatment which destabilises MTs. In this case VP22 also stabilised MTs against depolymerisation by 4 deg C. incubation. The stabilisation of MTs by VP22 makes it possible to use VP22 proteins in applications such as retarding the growth of cells, e.g. in the treatment of proliferative disorders.

It has also been found that the stabilisation of MTs by VP22 is associated with acetylation of the MTs. Acetylation of MTs was previously reported as a marker for MT stability (Piperno et al, J Cell Biol 104 (1987) 289–302). This has been shown by use of monoclonal antibody specific for the acetylated form of tubulin (obtainable from Sigma Chemical), in colocalisation assays by immunofluorescence, and by Western blot assays. This effect can be used as a biochemical marker for analysing and quantitating the level of MT stabilisation induced by VP22 or a variant or derviative thereof.

It has further been found that a fusion between VP22 and green fluoresecent protein (GFP), as described in WO 97/05265, is also, like wild-type VP22 protein, capable of stabilising MTs, thus allowing convenient fluorescence monitoring procedures including fluorecence microscopy to monitor the MT stabilisation and its effects.

By time-lapse confocal microscopy of single cells expressing GFP-VP22 fusion protein it has been determined that such cells containing VP22-induced MT bundles are unable to proceed through normal cell division, and appear to have had their MTs stabilised against the depolymerisation step required for the formation of mitotic spindles at stage G2/M of the cell cycle. Cell death has been observed in GFP-VP22-affected cells in which the cell cycle has been so arrested. Accordingly VP22 appears to have utility as a spindle poison with effects similar to those of the antineoplastic compounds taxol and its derivatives, referred to above.

Identification of the Region of VP22 Involved in Interacting with MTs.

To broadly identify the region of VP22 involved in MT interaction, we utilised a range of C terminal deletion mutants of the protein. The plasmids encoding WT, del-267, del-192 and del-119 (FIG. 3a) forms of VP22 were transfected into COS 1 cells and analysed by immunofluorescence using the anti VP22 antibody AGV30. The del-267 and del-119 constructs comprise respectively aminoacids 1–267 inclusive, and aminoacids 1–119 inclusive of the wild type sequence of VP22 of HSV1 as disclosed in above-cited WO 97/05265 and references cited therein. The del-192 construct consists of aminoacids 1–191 inclusive plus a residue 192 mutated to leucine.

Figure 3:
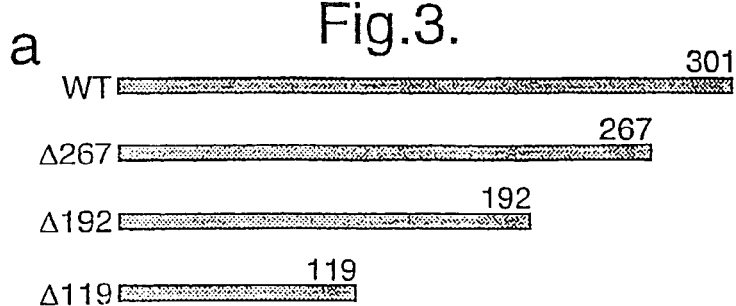
FIG. 3a shows schematically a series of C-terminal deletion mutants of VP22 which were transfected in COS-1 cells and their ability to bundle MT determined.
FIGS. 3b–3e show the localisation patterns obtained using immunofluorescence to assess MT bundling.
Figure 3:
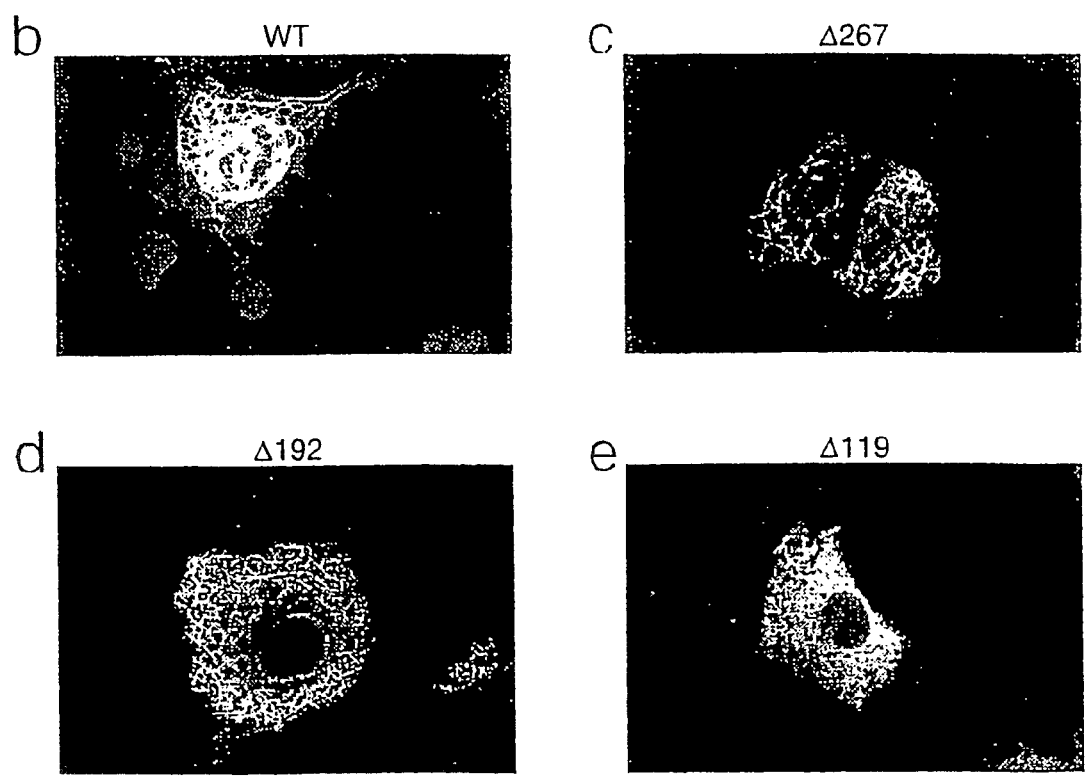

As previously observed, WT gave the typical localisation pattern of a central cell with VP22 in cytoplasmic filaments, surrounded by cells with VP22 in their nuclei (FIG. 3b). While the del-267 mutant did not have the ability to move between cells (see previous patent applications), it still retained the property of MT bundling (FIG. 3c).

Likewise, del-192 was also capable of bundling MTs (FIG. 3d), although it was not as efficient as either WT or del-267. However, removal of a further 73 residues from the C terminus of VP22 resulted in a protein which localised in a cytoplasmic diffuse pattern and which did not form cytoplasmic filaments (FIG. 3e).

Thus, these results show that the region of VP22 involved in MT association lies between residues 119 and 192, or that the deletions in this region disrupt the structure of the VP22 determinant responsible for the MT binding.

Thus it has been found that for example variant VP22 proteins consisting of residues 1–172 of the native VP22 of HSV1, or of residues 1–192 (with aa192 modified to leucine), or 1–267, retain in some degree the ability to bundle microtubules as decribed herein. In these examples the longer sequences have increasing efficiency. It was also found that the VP22 fragments consisting of 1–119 or 1–159 did not appear to retain the MT-bundling activity. A mutant with a regional deletion of residues 160–173 and in their place three 'spacer' residues his, gly and pro was found to have substantially reduced effectiveness of MT binding.

The initial localisation of the determinant of VP22 responsible for binding MTs makes it possible to engineer VP22 variants in which the MT binding property is reduced or eliminated altogether, e.g. to provide variants having improved transport efficiency.

The experiments described above provide methods that can be employed to determine when binding of VP22 proteins or MTs occurs. By way of example, localisation patterns obtained using the anti-tubulin and anti-VP22 antibodies can be used to determine whether VP22 variants or derivatives have one of the MT binding properties discussed above.

Among the homologues of herpesviral VP22 that can be used in the present invention are for example the homologues of HSV1-VP22 in other herpesviruses such as HSV type 2 (HSV2), bovine herpesvirus (BHV), and Marek's disease virus (MDV), and the derivatives of such homologues analogous to the derivatives discussed above.

The invention extends to modifications and variations that will be apparent to the reader skilled in the art, and in particular extends to combinations and subcombinations of the features mentioned or described herein and in specification WO 97/05265. The documents cited herein are all hereby expressly incorporated in their entirety by reference.

The invention claimed is:

1. A method of delivering a substance to microtubules, comprising exposing said microtubules to said substance, said substance being in a form selected from the group consisting of a fusion, a covalent coupling, and a non-covalent coupling, of said substance with a protein, wherein said protein is a herpes simplex virus 1 (HSV1) VP22 protein, or is a portion thereof comprising amino acids 1 to 267 of HSV1 VP22 protein, amino acids 1 to 191 of HSV1 VP22 protein, or amino acids 1 to 172 of HSV1 VP22 protein, and wherein said substance is a microtubule binding substance.

2. The method of claim 1, wherein the substance is taxol.

3. The method of claim 1, wherein said protein comprises amino acids 1 to 267 of HSV1 VP22 protein.

4. The method of claim 1, wherein said protein comprises amino acids 1 to 191 of VP22 protein.

5. The method of claim 1, wherein said protein comprises amino acids 1 to 172 of VP22 protein.

* * * * *